Nov. 25, 1952 E. H. BARCAFER Plant Pat. 1,151
PEPEROMIA PLANT
Filed Nov. 19, 1951
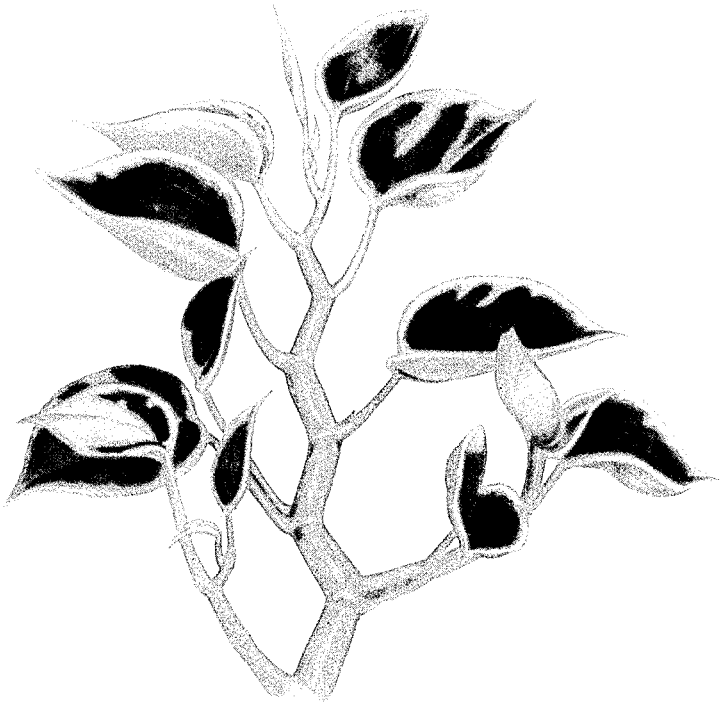
INVENTOR
ELLIS H. BARCAFER
BY Toulmin & Toulmin
ATTORNEYS Patented Nov. 25, 1952

Plant Pat. 1,151

UNITED STATES PATENT OFFICE 1,151

PEPEROMIA PLANT

Ellis H. Barcafer, Springfield, Ohio

Application November 19, 1951, Serial No. 256,990

1 Claim. (Cl. 47—59)

My present discovery relates to a new and distinct variety of Peperomia plant which originated as a sport of a Scandens in my greenhouses at Springfield, Ohio. I have reproduced the new variety asexually by cuttings in the same greenhouses in approximately thirty specimens and the characteristics of the new variety have proved to be permanent.

The parent Peperomia Scandens is an upright, relatively fast growing plant and is an all-over medium dark green in color with no marked variegated coloring in the leaves, veins or stem.

This new variety is distinctly and outstandingly different from the parent variety especially with regard to its leaf coloring and formation, the vein and stem coloring, and its slower compact growth which produces by natural means a bushy plant.

The leaves of my new variety are variegated by an array of three contrasting colors; the marginal border is distinctively yellowish white in vivid contrast with a medium green central area splashed with irregular patches of grey-green. The marginal border is irregular and in some instances the yellowish white coloration extends well into the leaf, the abrupt transition to the medium green producing a very pleasing over-all effect. The small splashes of grey-green occur irregularly along the main vein of the leaf as well as in the body of the leaf, and some of the patches form a transition phase between the medium green and the yellowish white marginal area.

This new variety thrives as a house plant and the noted bushiness of growth together with the pronounced coloring and leaf formation make this a most attractive and decorative plant.

The illustration accompanying this specification shows in approximately true color, my new Peperomia, and the following is a detailed description of this new variety and in which description reference is made to the Maerz and Paul Dictionary of Color.

This new variety attains in the main stem an upright growth in the early stages of about 6 to 8 inches, becoming thereafter distinctly bushy. This compactness and growth is attained through the tendency of the plant to spread laterally and is also due in considerable measure to the relative shortness of the spacing between the nodal joints, that is about ⅜ to ½ inch, which is about one-half that of the parent. The compactness is further due, though to a somewhat lesser extent, to the petiole length which is between 1 to 2 inches; compactness is also attained due to the distinct self-branching characteristic, enabling the plant to produce at many of the nodal joints small leaves having the same variegation as the larger leaves. The plant growth is relatively slow the rate being about one-half of the parent in the early stages.

One of the most outstanding features of the new variety is the cup-shaped appearance of the leaves; the leaves are lobular in form and of somewhat greater length than width in their natural position, a typical leaf having a length of about 2 inches and a width of about 1½ inches. This width measurement is taken in the natural or cupped position from edge to edge of the leaf and the measurement will be about 0.1 inch greater if the leaf is flattened and then measured at the same edge points. The degree of cupping or upward curvature of the leaf varies and may in given instances be somewhat greater or less than that indicated by these figures but to the eye the leaf always has a pronounced "cup-shape."

There are five primary veins in the leaf which run from the base of the leaf to the tip end; the central vein passing in substantially a straight line between these termini, while on either side of this central vein two veins pass through each lobular part and between the same termini. The inner veins of these latter veins do not in general extend laterally of the leaf sufficiently to pass into the light colored marginal portions, although the outer two of the veins in some instances intersect the grey-green and marginal portions of the leaves.

The color characteristics of my new variety according to Maerz and Paul Dictionary of Color are shown in the following table:

| | Plate | Letter | Number |
|---|---|---|---|
| Outside border of the leaf | 17 | G | 3 |
| Central area of leaf | 22 | H | 8 |
| Splashes of grey-green | 22 | H | 3 |
| Darkest color of border | 17 | J | 2 |
| Back of leaf | 17 | D | 5 |
| Petiole | 18 | E | 5 |
| Stem | 18 | D | 6 |

The new variety has no reproductive organs and does not reproduce fruit or flowers.

The new variety is distinct from the parent the leaves of which are solid green; the stem of which is dark green similar to the leaf; the leaf of which does not have a pronounced cup-shape; the growth rate of which is about twice that of the new variety; and the compactness of which is less than that of the new variety.

Having thus disclosed my invention, I claim:

A new and distinct variety of Peperomia plant, as herein shown and described, characterized particularly by its compact branching growth; its habit of growing first upright and later spreading laterally; the cup-shaped appearance of the leaves; and by the conspicuous variegated coloring of its leaves, comprising an irregular marginal area of a shade of yellowish white surrounding a larger central area of medium green, splashed with patches of grey-green, some of which patches form a transition phase between the medium green and the yellowish white marginal area.

ELLIS H. BARCAFER.

No references cited.